(12) United States Patent
Edwards (10) Patent No.: US 11,257,037 B2
(45) Date of Patent: Feb. 22, 2022

(54) GRAPHICAL REPRESENTATIONS OF TIME-ORDERED DATA

(71) Applicant: CERNER INNOVATION, INC., Kansas City, KS (US)

(72) Inventor: David Lee Edwards, Kansas City, MO (US)

(73) Assignee: Cerner Innovation, Inc., North Kansas City, MO (US)

( * ) Notice: Subject to any disclaimer, the term of this patent is extended or adjusted under 35 U.S.C. 154(b) by 1137 days.

(21) Appl. No.: 15/810,955

(22) Filed: Nov. 13, 2017

(65) Prior Publication Data

US 2018/0068408 A1 Mar. 8, 2018

Related U.S. Application Data

(63) Continuation of application No. 13/860,030, filed on Apr. 10, 2013, now abandoned.

(60) Provisional application No. 61/783,356, filed on Mar. 14, 2013.

(51) Int. Cl.
*G06Q 10/10* (2012.01)
*G16H 10/60* (2018.01)

(52) U.S. Cl.
CPC ............ *G06Q 10/10* (2013.01); *G16H 10/60* (2018.01)

(58) Field of Classification Search
CPC ............................... G06Q 10/10; G16H 10/60
See application file for complete search history.

(56) References Cited

U.S. PATENT DOCUMENTS

| | | | |
|---|---|---|---|
| 2004/0172558 A1 | 9/2004 | Callahan et al. | |
| 2008/0081594 A1* | 4/2008 | Lee | H04M 1/72427 455/412.2 |
| 2008/0109870 A1 | 5/2008 | Sherlock et al. | |
| 2010/0275263 A1* | 10/2010 | Bennett | G06F 21/577 726/25 |
| 2011/0216067 A1* | 9/2011 | Schorr | G06F 3/0486 345/440 |
| 2012/0041769 A1* | 2/2012 | Dalal | G06Q 10/101 705/1.1 |
| 2013/0046786 A1* | 2/2013 | Fabbri | G16H 10/60 707/776 |

(Continued)

OTHER PUBLICATIONS

Oxygen Forensic Suite 2012 v.4.4, Oxygen Forensic Suite 2012 v.4.4 release notes. Release date: Jul. 27, 2012. Accessed Mar. 27, 2015. <http://www.oxygen-forensic.com/download/whatsnew/OFS2012v44ReleaseNotes.pdf> (Year: 2012).*

(Continued)

*Primary Examiner* — Jonathan Durant
(74) *Attorney, Agent, or Firm* — Shook, Hardy & Bacon LLP (57) ABSTRACT

Methods, systems, and computer-storage media are provided for generating graphical representations of audit events. A party-of-interest is represented by a central node, and one or more peripheral nodes surrounding the central node represent parties having electronic records accessed by the party-of-interest during a selected time frame. The size of the peripheral nodes represents a frequency of access of the node's respective electronic record. Each of the peripheral nodes is actionable enabling a user to view information related to the audit event.

20 Claims, 5 Drawing Sheets

(56) References Cited

U.S. PATENT DOCUMENTS

2013/0097662 A1* 4/2013 Pearcy .................. G06F 21/554
726/1
2013/0326579 A1* 12/2013 Bhatti .................... H04L 63/20
726/1

OTHER PUBLICATIONS

Oxygen Forensic Suite 2012 v.4.4, Oxygen Forensic Suite 2012 v.4.4 release notes. Release date: Jul. 27, 2012. Accessed Mar. 27, 2015. <http://www.oxygen-forensic.com/download/whatsnew/OFS2012v44ReleaseNotes.pdf>.

* cited by examiner

GRAPHICAL REPRESENTATIONS OF TIME-ORDERED DATA

CROSS-REFERENCE TO RELATED APPLICATIONS

This application is a continuation application of, and claims the benefit of priority of, co-pending U.S. patent application Ser. No. 13/860,030, filed Apr. 10, 2013 and entitled "Graphical Representations of Time-Ordered Data," which claims the benefit of priority of U.S. Provisional Application No. 61/783,356, filed Mar. 14, 2013 and entitled "Graphical Representations of Time-Ordered Data." The entireties of the aforementioned applications are incorporated by reference herein.

BACKGROUND

In order to comply with laws governing information security, such as the Health Insurance Portability and Accountability Act (HIPAA), certain institutions must maintain audit logs that track how often customer electronic records are accessed, the reasons for accessing the records (e.g., documentation, modification, etc.), and the identities of users who are accessing the electronic records. Examples of institutions include healthcare facilities, financial institutions, educational institutions, and the like.

Most commercial tools for querying audit logs employ some form of report generation based loosely on the concept of relational queries. Many of the reports are batch-oriented in nature because of the computational and input/output demands necessary to conduct the underlying queries. As well, these reports are often presented in the form of two-dimensional tables. While these reports may be sufficient to meet information security requirements, they are not necessarily intuitive and efficient for end users nor do they facilitate the exploration of audit events related to a particular user.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

In brief and at a high level, this disclosure describes, among other things, methods, systems, and computer-storage media for presenting graphical representations of time-ordered audit events. The time-ordered audit events may represent instances where customer electronic records have been accessed by a party-of-interest during a specified time frame. The electronic records may include financial records, educational records, health records, insurance records, and the like.

In one aspect, the party-of-interest is a clinician and the audit events represent instances where the clinician has accessed patient electronic medical records (EMRs). For example, a healthcare facility may become suspicious of the activities of the clinician, or a patient may have filed a complaint alleging some sort of privacy breach. In response to either of these two situations, the healthcare facility may wish to view an audit log of EMR accesses during a specified time frame and details associated with each access. An intuitive and easy-to-use graphical user interface (GUI) is needed to facilitate this process.

As such, the present invention provides for a GUI that utilizes, in one aspect, timelines that enable a user to select a desired time frame, a central node representing the party-of-interest, and one or more peripheral nodes representing parties having electronic records that have been accessed by the party-of-interest during the selected time frame. As used throughout this application, the term "party-of-interest" refers to a person employed or associated with a facility maintaining an audit log and who has access rights to electronic records kept by the facility. Exemplary parties-of-interest include clinicians, bank officers, teachers, administrators, and the like. The term "party" refers to an entity who receives services provided by the facility. As such, the party may refer to a customer, a patient, a student, and the like. The size of the peripheral nodes provides an indication of how frequently the electronic records were accessed. As well, both the central node and the peripheral nodes are actionable allowing a user to quickly gather information regarding, for example, the identity of the party-of-interest, the parties, and/or options for viewing additional information regarding the electronic record access.

In another aspect, the present invention provides for a GUI that utilizes one or more timelines configured to enable a user to select a time frame, a central node representing a party (e.g., a patient who is alleging a privacy breach), and one or more peripheral nodes representing parties-of-interest who have accessed the party's electronic records during the specified time frame. The size of the peripheral nodes indicates how frequently the party's electronic record was accessed by the node's respective party-of-interest Like above, both the central node and the peripheral nodes are actionable allowing a user to access information regarding, for example, the identity of the parties-of-interest, the party, and/or options for viewing additional information regarding the electronic record access.

In yet another aspect, the present invention provides for a GUI that utilizes one or more timelines configured to enable a user to select a desired time frame, a display area providing an indication of a party and a party-of-interest, and a clockwise timeline having one or more icons overlaid at different points in time; the bounds of the clockwise timeline correspond to the specified time frame. The icons represent different types of audit events associated with the party and the party-of-interest. For instance, using healthcare as an example, one audit event may be the clinician accessing the patient's EMR to order a medication, while another audit event may be the clinician accessing the patient's EMR to document a clinical note. The icons are actionable, and interaction with an icon can initiate the presentation of a summary of the associated audit event.

BRIEF DESCRIPTION OF THE DRAWINGS

Embodiments are described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention are directed to methods, systems, and computer-storage media for presenting graphical representations of time-ordered audit events. The time-ordered audit events may represent instances where electronic records associated with one or more parties have been accessed by a party-of-interest during a specified time frame. As mentioned, the term "party-of-interest" refers to a person employed or associated with a facility maintaining an audit log and who has access rights to electronic records kept by the facility. Exemplary parties-of-interest include clinicians, bank officers, administrators, teachers, and the like. The term "party" refers to an entity who receives services provided by the facility. As such, the party may refer to a customer, a patient, a student, and the like. The electronic records may include financial records, educational records, health records, insurance records, and the like.

Figure 1:
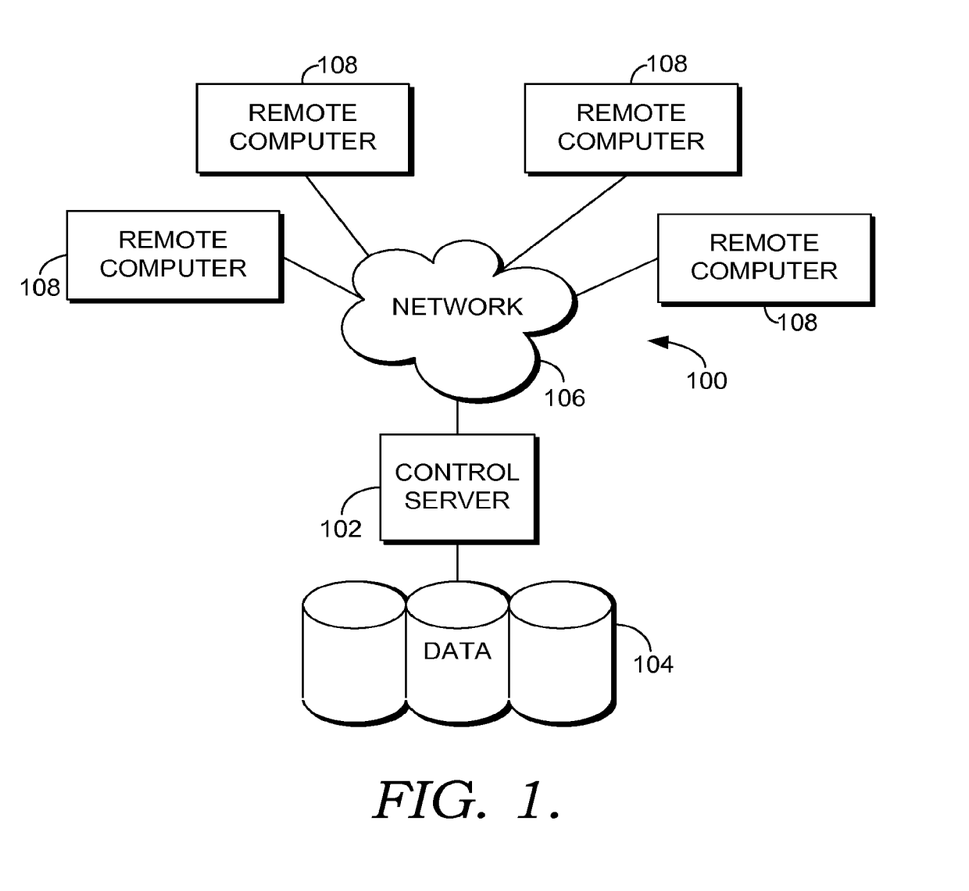
FIG. 1 is a block diagram of an exemplary computing environment suitable to implement embodiments of the present invention.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of non-transitory computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
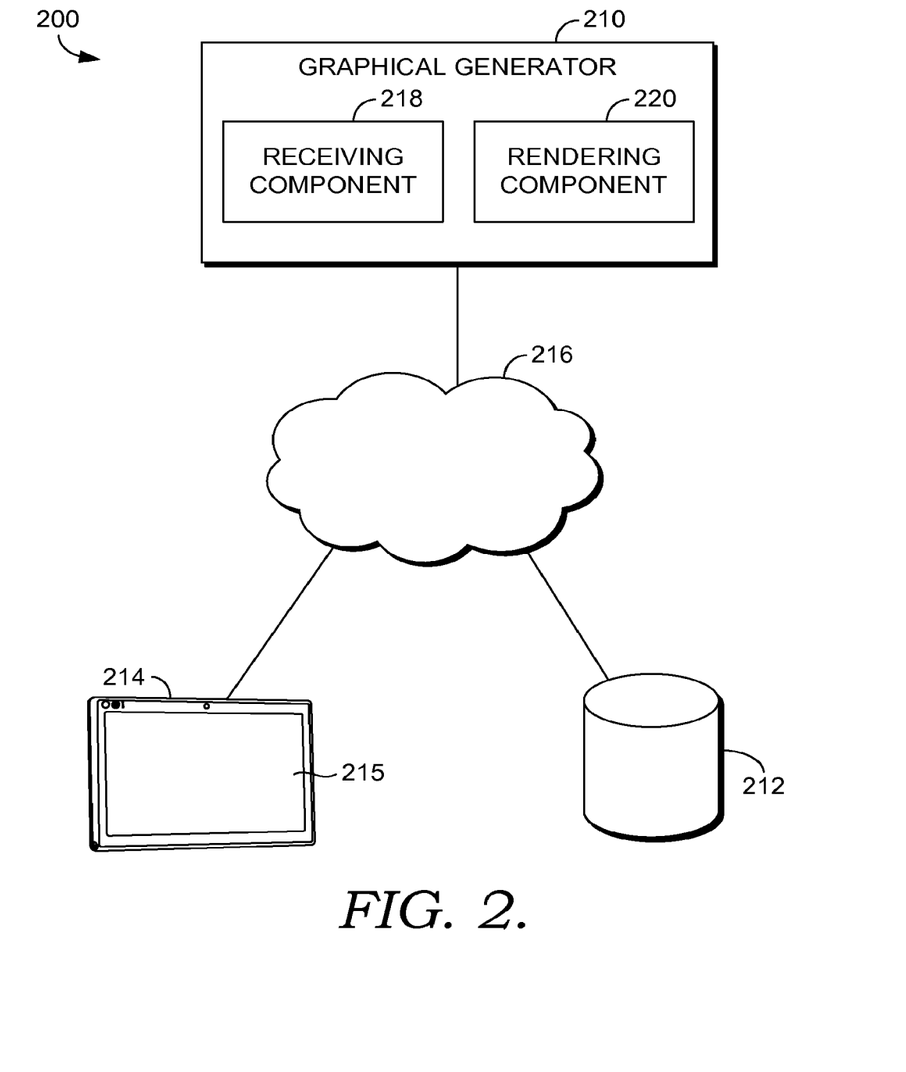
FIG. 2 is a block diagram of an exemplary system for visually representing time-ordered data related to a party-of-interest suitable to implement embodiments of the present invention.

Turning now to FIG. 2, an exemplary computing system environment 200 is depicted suitable for use in implementing embodiments of the present invention. The computing system environment 200 is merely an example of one suitable computing system environment and is not intended to suggest any limitation as to the scope of use or functionality of embodiments of the present invention. Neither should the computing system environment 200 be interpreted as having any dependency or requirement related to any single module/component or combination of modules/components illustrated therein.

The computing system environment 200 includes a graphical generator 210, a data store 212, and an end-user computing device 214 all in communication with one another via a network 216. The network 216 may include, without limitation, one or more local area networks (LANs) or wide area networks (WANs). The network 216 may be a secure network associated with a facility such as a healthcare facility, a financial institution, an educational institution, and the like. The secure network 216 may require that a user log in and be authenticated in order to send and/or receive information over the network 216.

In some embodiments, one or more of the illustrated components/modules may be implemented as stand-alone applications. In other embodiments, one or more of the illustrated components/modules may be integrated directly into the operating system of the graphical generator 210. The components/modules illustrated in FIG. 2 are exemplary in nature and in number and should not be construed as limiting. Any number of components/modules may be employed to achieve the desired functionality within the scope of embodiments hereof. Further, components/modules may be located on any number of servers. By way of example only, the graphical generator 210 might reside on a server, a cluster of servers, or a computing device remote from one or more of the remaining components.

It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components/modules, and in any suitable combination and location. Various functions described herein as being performed by one or more entities may be carried out by hardware, firmware, and/or software. For instance, various functions may be carried out by a processor executing instructions stored in memory.

The data store 212 is configured to store information for use by, for example, the graphical generator 210 and/or the end-user computing device 214. The information stored in association with the data store 212 is configured to be searchable for one or more items of information stored in association therewith. The information stored in association with the data store 212 may comprise general information used by the graphical generator 210 and/or the end-user computing device 214.

In one aspect, the data store 212 may store audit logs kept by an entity. As used throughout this application, the term "audit log" or "audit trail" refers to chronological records of system activities that enable the reconstruction and examination of the sequence of events and/or changes in an event. More specifically, the term audit log may refer to chronological records of customer electronic record access and details associated with such access. As described above, the entity may include financial institutions, educational institutions, healthcare facilities, and the like.

With respect to healthcare facilities, in addition to audit logs, the data store 212 may store electronic medical records (EMRs) of patients associated with the healthcare facility. EMRs may comprise electronic clinical documents such as images, clinical notes, orders, summaries, reports, analyses, or other types of electronic medical documentation relevant to a particular patient's condition and/or treatment. Electronic clinical documents contain various types of information relevant to the condition and/or treatment of a particular patient and can include information relating to, for example, patient identification information, images, alert history, culture results, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, and a host of other relevant clinical information.

The content and volume of such information in the data store 212 are not intended to limit the scope of embodiments of the present invention in any way. Further, though illustrated as a single, independent component, the data store 212 may, in fact, be a plurality of storage devices, for instance, a database cluster, portions of which may reside on the graphical generator 210, the end-user computing device 214, and/or any combination thereof.

As shown, the end-user computing device 214 includes a display screen 215. The display screen 215 is configured to display information to the user of the end-user computing device 214, for instance, information relevant to communications initiated by and/or received by the end-user computing device 214, graphical representations of audit events, and/or the like. Embodiments are not intended to be limited to visual display but rather may also include audio presentation, combined audio/visual presentation, and the like. The end-user computing device 214 may be any type of display device suitable for presenting a graphical user interface. Such computing devices may include, without limitation, a computer, such as, for example, any of the remote computers 108 described above with reference to FIG. 1. Other types of display devices may include tablet PCs, PDAs, mobile phones, smart phones, as well as conventional display devices such as televisions. Interaction with the graphical user interface may be via a touch pad, a pointing device, and/or gestures.

Components of the graphical generator 210 may include a processing unit, internal system memory, and a suitable system bus for coupling various system components, including one or more data stores for storing information (e.g., files and metadata associated therewith). The graphical generator 210 typically includes, or has access to, a variety of computer-readable media.

The computing system environment 200 is merely exemplary. While the graphical generator 210 is illustrated as a single unit, it will be appreciated that the graphical generator 210 is scalable. For example, the graphical generator 210 may in actuality include a plurality of computing devices in communication with one another. Moreover, the data store 212, or portions thereof, may be included within, for instance, the graphical generator 210 as a computer-storage medium. The single unit depictions are meant for clarity, not to limit the scope of embodiments in any form.

As shown in FIG. 2, the graphical generator 210 comprises a receiving component 218 and a rendering component 220. In some embodiments, one or more of the components 218 and 220 may be implemented as stand-alone applications. In other embodiments, one or more of the components 218 and 220 may be integrated directly into the operating system of a computing device such as the remote computer 108 of FIG. 1. It will be understood that the components 218 and 220 illustrated in FIG. 2 are exemplary in nature and in number and should not be construed as limiting. Any number of components may be employed to achieve the desired functionality within the scope of embodiments hereof.

The receiving component 218 is configured to receive user selections, commands, filters, requests, or inputs. User selections and/or requests may include requests for graphical representations of audit events. Further, the user is able to select different views of the audit events. For instance, one request may be for a graphical representation of electronic records accessed by a party-of-interest during a specified time frame. Another request may be for a graphical representation of all parties-of-interest who have accessed a specified party's electronic records during a specified time frame. An additional request may be for a graphical representation of a detail view of audit events relating to a specified party-of-interest and a party.

The rendering component 220 is configured to utilize audit logs stored in association with the data store 212 in order to respond to the requests received by the receiving component 218. As such, the rendering component 220 is configured to render graphical representations of audit events on a graphical user interface (GUI) that may be presented on the display screen 215 of the end-user computing device 214.

Figure 3:
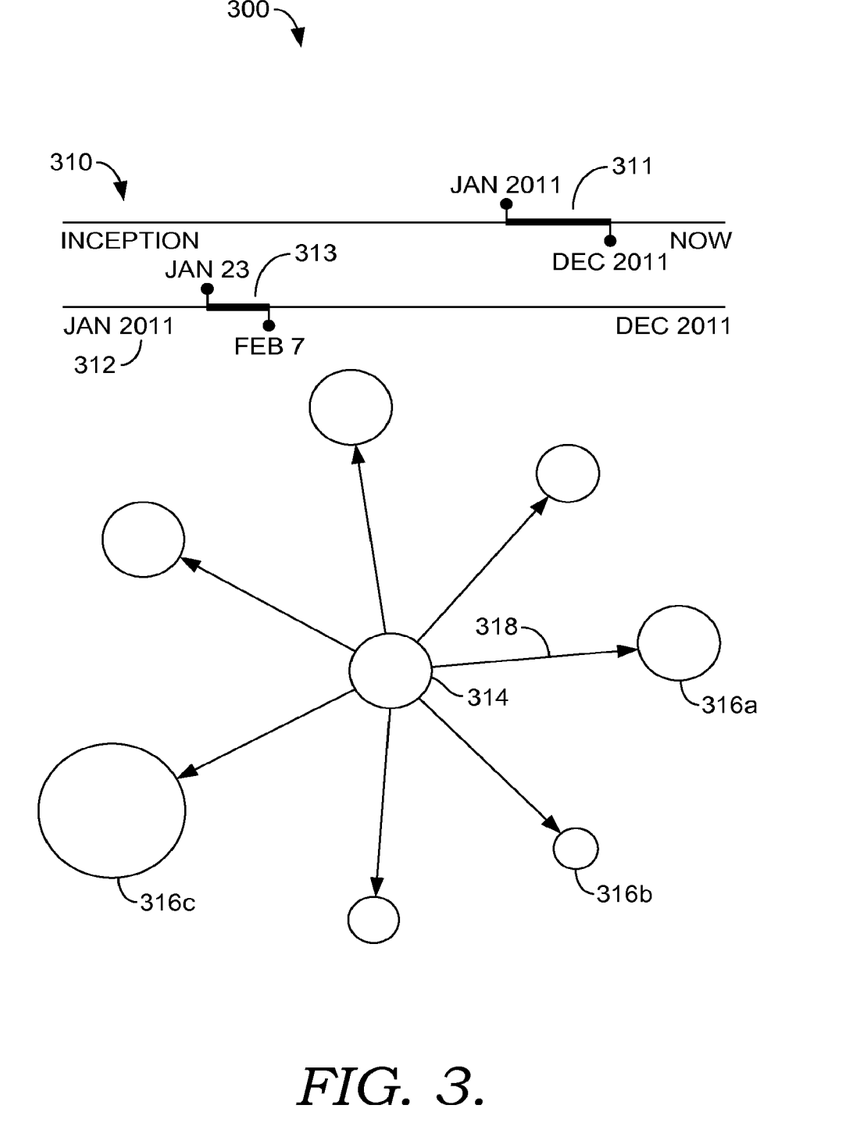
FIG. 3 is an exemplary graphical user interface having a central node representing a party-of-interest and one or more peripheral nodes representing parties having electronic records accessed by the party-of-interest during a specified time frame in accordance with an embodiment of the present invention.
Figure 4:
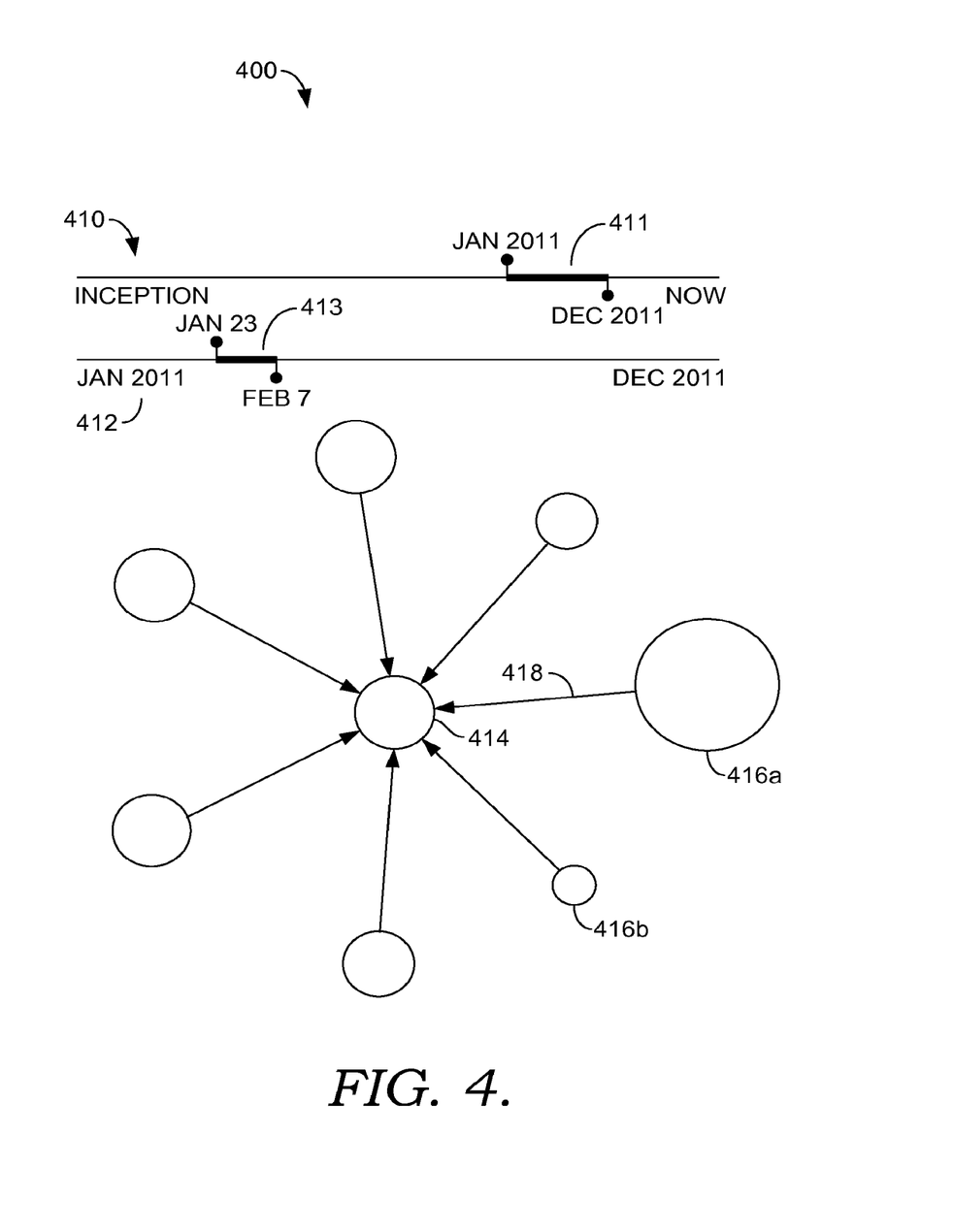
FIG. 4 is an exemplary graphical user interface having a central node representing a party and one or more peripheral nodes representing parties-of-interest who have accessed electronic records associated with the party during a specified time frame in accordance with an embodiment of the present invention.
Figure 5:
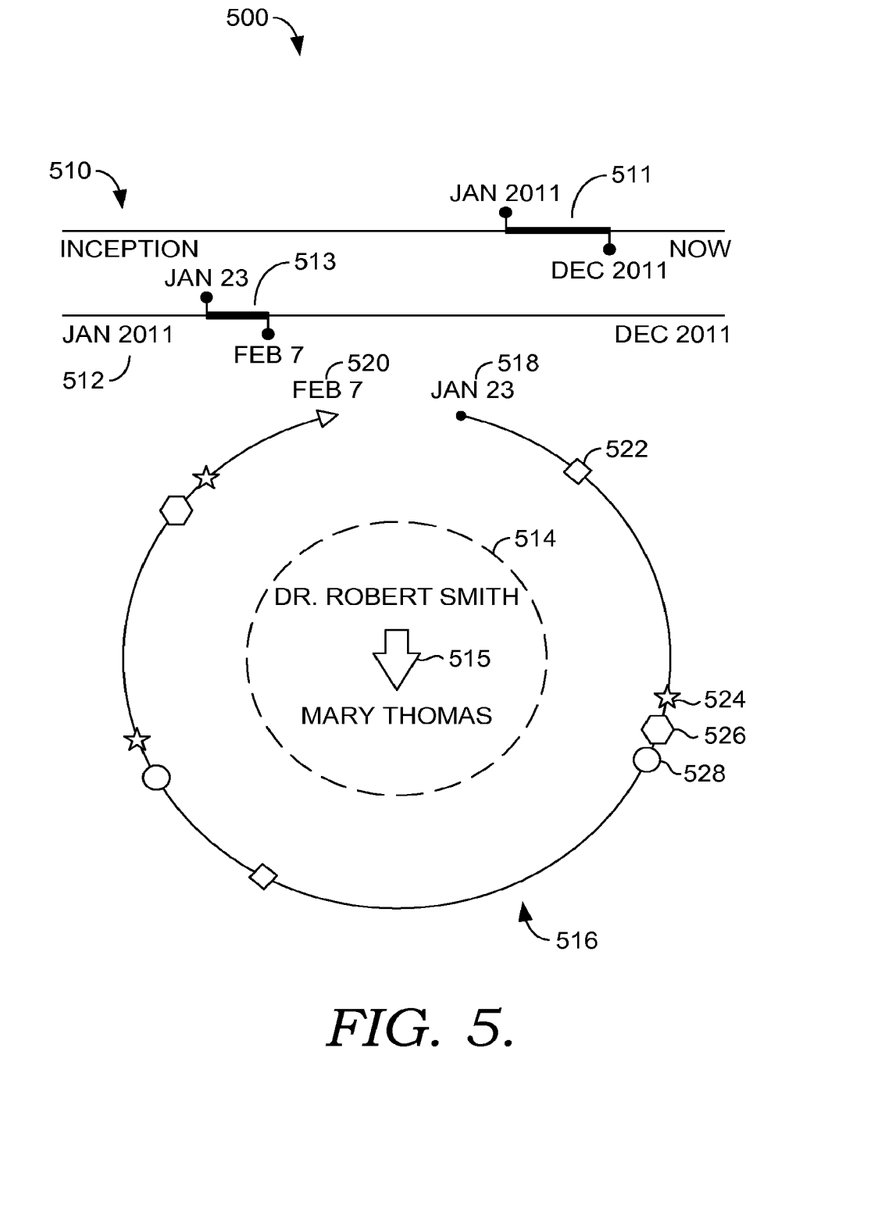
FIG. 5 is an exemplary graphical user interface having a clockwise timeline with icons overlaying points in time corresponding to audit-type events between a party and a party-of-interest in accordance with an embodiment of the present invention.

Turning now to FIGS. 3-5, FIGS. 3-5 depict exemplary GUIs illustrating the presentation of graphical representations of audit events. FIG. 3 depicts a GUI 300 in which the party-of-interest is represented by a central node 314 and one or more peripheral nodes, e.g., nodes 316a, 316b, and 316c, surrounding the central node 314 represent parties having electronic records accessed by the party-of-interest during a specified time frame. Although only the nodes 316a-c are numbered and referenced in the GUI 300, the following discussion is applicable to all of the peripheral nodes shown in the GUI 300. The GUI 300 may be especially useful in situations where a facility suspects that a party-of-interest may be in violation of information security requirements.

The party-of-interest represented by the central node 314 and the parties represented by the peripheral nodes 316a-c may be represented by circles as shown. Other ways of representing the party-of-interest and the parties are contemplated. For example, the nodes 314 and/or 316a-c may be represented by other geometric shapes such as squares, triangles, ovals, diamonds, and the like. Additionally, the nodes 314 and/or 316a-c may be represented by stylized icons corresponding to a person, or a picture of the party or party-of-interest represented by the node. Any and all such variations, and any combination thereof, are contemplated as being within the scope of the invention. As well, depending on the amount of available screen real estate, the party-of-interest and/or the parties' names may be presented in association with the nodes 314 and/or 316a-c.

Arrows, such as arrow 318 indicate a direction of access. For example, the arrow 318 indicates that the party-of-interest represented by the central node 314 accessed the electronic record of the party represented by the peripheral node 316a instead of vice versa.

The GUI 300 further includes timelines 310 and 312. The timeline 310 represents a coarse-grained timeline covering a time period from the inception of the audit log to the current point in time. The timeline 310 includes a bi-directional slider 311 that enables a user to select a time period in months and years. The timeline 312 represents a fine-grained timeline having a range corresponding to the range selected by the slider 311 on the coarse-grained timeline 310. The timeline 312 includes a bi-directional slider 313 that enables a user to select a time period in months and days. The use of timelines 310 and 312 enables a user to quickly narrow in on the time period in question.

Changing the specified time frame using either the bi-directional slider 311 and/or the bi-directional slider 313 causes the number of peripheral nodes presented on the GUI 300 to automatically update in real time. For example, a user may initially select a time frame corresponding to Apr. 1, 2011-May 1, 2011. In response to the selection, a first set of peripheral nodes is presented corresponding to parties having electronic records accessed during the selected time frame by the party-of-interest represented by the central node 314. The user may then select a time frame corresponding to Apr. 1, 2011-Aug. 1, 2011. The number of peripheral nodes may dynamically increase because the number of electronic records accessed by the party-of-interest would likely be greater since the time span is longer.

The size of the peripheral nodes, such as the peripheral nodes 316a, 316b, and 316c, represents the frequency with which the node's respective electronic record was accessed by the party-of-interest. In one aspect, a larger-sized node indicates a greater frequency of access and a smaller-sized node indicates a lesser frequency of access. Thus, with respect to FIG. 3, the party's electronic record associated with the peripheral node 316c has been accessed at a higher frequency than the electronic records associated with the peripheral nodes 316a and 316b. In another aspect, a larger-sized node indicates a lesser frequency of access and a smaller-sized node indicates a greater frequency of access. Any and all such aspects, and any combination thereof, are contemplated as being within the scope of the invention.

Each of the nodes 314 and 316a-c is actionable. Interaction via, for example, hovering over the central node 314 and/or peripheral nodes 316a-c may initiate the presentation of user-identifying information for the party and/or party-of-interest represented by the node. With respect to the party-of-interest represented by the central node 314, user-identifying information may include name, role description, access rights associated with the party-of-interest, how long the party-of-interest has been associated with the company maintaining the audit logs, and the like. With respect to the parties represented by the peripheral nodes 316a-c, user-identifying information may include name, date-of-birth, address, gender, identifiers (e.g., customer ID), date of service, and the like.

Selection via, for example, a right or left mouse click and/or a tapping gesture of a peripheral node such as the peripheral node 316a, may automatically initiate a new GUI such as the GUI shown in FIG. 4, or may initiate the presentation of a set of options. One option may be for the presentation of a GUI where the party represented by the selected peripheral node 316a is presented as the central node and peripheral nodes represent parties-of-interest who have accessed the party's electronic records during a specified time frame (e.g., the GUI shown in FIG. 4). Another option may be for the presentation of a GUI where details concerning the audit events between the party represented by the selected peripheral node 316a and the party-of-interest represented by the central node 314 are depicted on a circular timeline (e.g., the GUI shown in FIG. 5).

Although not shown, the GUI 300 may also include an area that presents one or more filters. Selection of a filter restricts the peripheral nodes to those nodes that meet the filter criteria. Exemplary filters may include filters based on the gender of the party represented by the peripheral nodes, filters corresponding to party roles (employee, customer, etc.), filters corresponding to specific types of audit events such as accessing an electronic record to place an order, make a change to a document, or create a new document, filters based on location such as the venue or facility in which the audit event took place, filters corresponding to a IP address or a device ID that indicate the device used to access the electronic record, and/or customized filters. A displayed filter may be presented in association with a numerical indicator (displayed adjacent to the filter name) that provides an indication of the number of results in the result set for that filter. For instance, "Female (17)" indicates that there are 17 results in the result set for the female filter. Using healthcare as an example, a healthcare facility may suspect that Clinician A is improperly prescribing narcotic medications. The healthcare facility may select a medication filter that restricts the peripheral nodes to those patients whose EMRs were accessed by Clinician A in order to prescribe narcotic medications.

Turning now to FIG. 4, FIG. 4 depicts a GUI 400 where a central node 414 represents a party and one or more peripheral nodes surrounding the central node 414, e.g., peripheral nodes 416a and 416b, represent parties-of-interest who have accessed the party's electronic record during a specified time frame. Although only the peripheral nodes 416a and 416b are numbered and referenced in the GUI 400, the discussion that follows is applicable to all of the peripheral nodes shown in the GUI 400. The GUI 400 may be presented in response to a selection of one of the options discussed with respect to the GUI 300 (e.g., the options that are presented when a user selects or otherwise interacts with one of the peripheral nodes 316a-c). The GUI 400 may be especially useful in those situations where the party represented by the central node 414 alleges a privacy breach, and the facility wishes to view parties-of-interest who have accessed the party's electronic records during a specified time frame. Arrows, such as arrow 418, represent the direction of access of the electronic record. For example, the arrow 418 indicates that the party-of-interest associated with the node 416a accessed the electronic record of the party represented by the central node 414 and not vice versa.

Like above, the party and the parties-of-interest may be represented by circles as shown. Other ways of representing the party and the parties-of-interest include other geometric shapes, icons, pictures, and the like. The name of the party and/or the parties-of-interest may be presented on the central node 414 and/or the peripheral nodes 416a-b when space permits.

The GUI 400 also includes timelines 410 and 412 similar to the timelines 310 and 312 of FIG. 3. The timelines 410 and 412 will reflect the same timeframes as those selected using the timelines 310 and 312 unless otherwise changed by the user. Thus, the timeline 410 represents a coarse-grained timeline covering a time frame from the inception of the audit log to the current point in time. The timeline 410 includes a bi-direction slider 411 that enables the selection of a time period in months and years. The timeline 412 represents a fine-grained timeline having a range corresponding to the range selected by the slider 411. The timeline 413 also includes a bi-directional slider 413 that enables the selection of a time period in days and months. Changing the specified time frame using the bi-directional sliders 411 and/or 413 causes the peripheral nodes to dynamically update to reflect the parties-of-interest that have accessed the party's electronic record during the new time frame.

The size of the peripheral nodes, such as the peripheral nodes 416a-b, reflects the frequency with which the partiesof-interest represented by the peripheral nodes 416a-b have accessed the party's electronic record. In one aspect, a larger-sized peripheral node indicates a greater frequency of access and a smaller-sized peripheral node indicates a lesser frequency of access. Thus, with respect to FIG. 4, the party-of-interest represented by the peripheral node 416a has accessed the party's electronic record more frequently than the party-of-interest represented by the peripheral node 416b. In another aspect, a smaller-sized peripheral node indicates a greater frequency of access and a larger-sized node indicates a lesser frequency of access. Any and all such variations, and any combination thereof, are contemplated as being within the scope of the invention.

Each of the nodes 414 and 416a-b is actionable. Interaction via, for example, hovering over the central node 414 and/or peripheral nodes 416a-b may initiate the presentation of user-identifying information for the party and/or party-of-interest represented by the node. With respect to the party represented by the central node 414, user-identifying information may include name, date-of-birth, address, gender, identifiers (e.g., customer ID), date of service, and the like. With respect to the parties-of-interest represented by the peripheral nodes 416a-b, user-identifying information may include name, role description, access rights associated with the party-of-interest, how long the party-of-interest has been associated with the company maintaining the audit log, and the like.

Selection via, for example, a right or left mouse click and/or a tapping gesture of a peripheral node such as the peripheral node 416a, may automatically initiate the presentation of a new GUI such as the GUI shown in FIG. 5, or may initiate the presentation of a set of options. One option may be for the presentation of a GUI corresponding to the GUI 300 where the central node represents the party-of-interest associated with the peripheral node 416a. Another option may be for the presentation of a GUI, such as the GUI shown in FIG. 5, where details concerning the audit events between the party represented by the central node 414 and the party-of-interest represented by the peripheral node 416a are depicted on a circular timeline.

The GUI 400 may also include filters (not shown). Selection of a filter restricts the peripheral nodes to those nodes that meet the requirements of the selected filter. The filters associated with the GUI 400 may be the same or different than the filters associated with the GUI 300. Exemplary filters may include gender filters, role filters, types of audit events, location filters, device or IP address filters, and/or customized filters. An additional filter that may be used in the context of the GUI 400 includes a filter that specifies parties-of-interest. Like above, a numerical indicator may be displayed alongside the filter name to provide an indication of the number of results in the result set for that filter.

FIG. 5 depicts a GUI 500 that presents a detailed view of audit events related to a specified party and a specified party-of-interest. The GUI 500 may be initiated in response to a selection of an option as described with respect to the GUI 300 or the GUI 400. The GUI 500 includes a first display area 514 that indicates the specified party and the specified party-of-interest (in this case, the specified party-of-interest is Dr. Robert Smith and the specified party is Mary Thomas). The party and the party-of-interest may be indicated by their respective names. Other ways of indicating the party and the party-of-interest may include icons or pictures. An arrow 515 in the first display area 514 depicts a direction of access. For example, the arrow 515 indicates that Dr. Robert Smith accessed patient Mary Thomas' EMR.

The GUI 500 also includes timelines 510 and 512 which are similar to the timelines 410 and 412 of FIG. 4 and the timelines 310 and 312 of FIG. 3. The timelines 510 and 512 represent the same timeframe as selected using the timelines 410 and 412 and/or the timelines 310 and 312 unless otherwise changed by the user. As such, the timeline 510 comprises a coarse-grained timeline that enables selection of a time period in months and years by using a bi-directional slider 511. Likewise, the timeline 512 represents a fine-grained timeline that enables selection of a time period in months and days using a bi-directional slider 513. Changing the time period using the bi-directional sliders 511 and/or 513 causes the GUI 500 to automatically update to reflect audit events corresponding to the new time period.

The GUI 500 further comprises a circular timeline 516 surrounding the first display area 514; the circular timeline 516 has bounds 518 and 520 corresponding to the time period selected by the bi-directional sliders 511 and 513. Overlaying the circular timeline 516 at distinct points in time are one or more icons, e.g., icons 522, 524, 526, and 528, representing one or more audit events that occurred at that respective point in time. Different types of audit events may be represented by different types of icons. For example, the icon 522 (e.g., a square) may represent an electronic record access to place an order, and the icon 524 (e.g., a star) may represent an electronic record access to modify an existing record. Likewise, the icon 526 (e.g., a hexagon) may represent an electronic record access to create a new document, and the icon 528 (e.g., a circle) may represent an electronic record access where no action was taken. A legend may be provided in association with the GUI 500 detailing the different type of audit events associated with the icons. The types of audit events described and the shape of the icons 522, 524, 526, and 528, are merely exemplary. Other types of audit events and other shapes of icons are contemplated and are within the scope of the current invention.

Hovering over or otherwise interacting with the icons 522, 524, 526, and 528, initiates a quick summary view of the audit event associated with the icon. For example, hovering over the icon 522 may initiate the summary "ordered ibuprofen 400 mg, b.i.d. on Jan. 26, 2011 at 8:43 am." Selecting an icon, such as the icon 522, may initiate a detailed view of the audit event. For example, selecting an icon may cause the presentation of the portion of the electronic record corresponding to the icon. Using the example above, selecting the icon 522 may initiate the presentation of the patient's EMR corresponding to the ordering event.

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. One or more non-transitory computer-storage media having computer-executable instructions embodied thereon that, when executed by a computing device, cause the computing device to perform a method for dynamically displaying information related to electronic records on a graphical user interface (GUI) and for facilitating an efficient and intuitive exploration of the electronic records related to information being dynamically displayed on the GUI, the method comprising:

receiving a first request for a graphical representation of information related to a set of electronic records associated with a party-of-interest or a party, wherein the party-of-interest is an individual having electronically accessed at least one electronic record in the set of electronic records and the party is an individual having an electronic record in the set of electronic records that has been electronically accessed by one or more parties-of-interest;

in response to receiving the first request, rendering the graphical representation on the GUI by utilizing data associated with the set of electronic records;

dynamically displaying on the GUI, a first timeline having a first range representing a first timeframe corresponding to a creation of the set of electronic records to a current point in time, the first timeline comprising a first coarseness and a first bi-directional slider configured to enable selection of a first time period within the first range;

dynamically displaying on the GUI, a second timeline having a second range representing the first time period selected with the first bi-directional slider on the first timeline, the second timeline comprising a second coarseness finer than the first coarseness of the first timeline and a second bi-directional slider configured to enable selection of a second time period within the second range, the second time period represented by a third range; and dynamically displaying on the GUI, an actionable central node representing either the party-of-interest or the party and a set of one or more actionable peripheral nodes at the first time period and the second time period selected with the first bi-directional slider and the second bi-directional slider, respectively, wherein, when the actionable central node is dynamically displayed as representing the party-of-interest, the set of one or more actionable peripheral nodes is dynamically displayed as representing a set of one or more parties, and wherein a size of each actionable peripheral node in the set of one or more actionable peripheral nodes represents a frequency of electronic access by the party-of-interest of an electronic record associated with a represented party in the set of one or more parties, and wherein, when the actionable central node is dynamically displayed as representing the party, the set of one or more actionable peripheral nodes is dynamically displayed as representing a set of one or more parties-of-interest, and wherein the size of each actionable peripheral node in the set of one or more actionable peripheral nodes represents a frequency of electronic access of the electronic record associated with the party by the party-of-interest represented by the each actionable peripheral node in the set of actionable peripheral nodes.

2. The media of claim 1, wherein a larger size of an actionable peripheral node in the set of one or more actionable peripheral nodes is associated with a greater frequency of electronic access of the electronic record associated with the represented party or party-of-interest.

3. The media of claim 1, wherein a smaller size of an actionable peripheral node in the set of one or more actionable peripheral nodes is associated with a lesser frequency of electronic access of the electronic record associated with the represented party or party-of-interest.

4. The media of claim 1, further comprising:
receiving a first selection of the first time period with the first bi-directional slider;
in response to receiving the first selection of the first time period, dynamically displaying the set of one or more actionable peripheral nodes as corresponding to the first time period,
receiving a second selection of the second time period with the second bi-directional slider; and
in response to receiving the second selection of the second time period, dynamically displaying the set of one or more actionable peripheral nodes as corresponding to the second time period.

5. The media of claim 1, further comprising one or more filters, each filter having a different criteria, selection of which restricts the set of one or more parties or the set of one or more parties-of-interest represented by the set of one or more actionable peripheral nodes.

6. The media of claim 1, wherein interaction with the actionable central node or an actionable peripheral node in the set of one or more actionable peripheral nodes initiates presentation of user-identifying information for the represented party or party-of-interest.

7. The media of claim 6, wherein the user-identifying information for the represented party comprises at least one of a name, date-of-birth, address, gender, or date of service.

8. The media of claim 6, wherein, the user-identifying information for the represented party-of-interest comprises at least one of a name, role description, or access rights.

9. The media of claim 1, wherein each actionable peripheral node in the set of one or more actionable peripheral nodes is connected to the actionable central node by an arrow, each arrow pointing in a direction of electronic access of the electronic record associated with the represented party or party-of-interest.

10. One or more non-transitory computer-storage media having computer-executable instructions embodied thereon that, when executed by a computing device, cause the computing device to perform a method for dynamically displaying an audit log history related to a clinician on a graphical user interface (GUI) and for facilitating an efficient and intuitive exploration of information related to the audit log history, the method comprising:
receiving a first request for a first graphical representation of audit events related to the audit log history and a set of electronic medical records (EMRs) accessed by the clinician;
in response to receiving the first request, rendering the first graphical representation on the GUI by utilizing data associated with the audit log history and the set of EMRs;
dynamically displaying on the GUI, a first timeline having a first range representing a first timeframe corresponding to a creation of the set of EMRs to a current point in time, the first timeline comprising a first coarseness and a first bi-directional slider configured to enable selection of a first time period within the first range;
dynamically displaying on the GUI, a second timeline having a second range representing the first time period selected with the first bi-directional slider on the first timeline, the second timeline comprising a second coarseness finer than the first coarseness of the first timeline, a second bi-directional slider configured to enable selection of a second time period within the second range, and a third range representing the second time period;
dynamically displaying on the GUI, an actionable central node representing the clinician and a set of one or more actionable peripheral nodes representing a set of patients associated with the set of EMRs;

receiving a selection of the first time period and the second time period; and in response to receiving the selection of the first time period and the second time period, dynamically displaying the set of one or more actionable peripheral nodes, wherein each actionable peripheral node represents a patient in the set of patients associated with an EMR in the set of EMRs accessed by the clinician during the selected first time period and the second time period, and wherein a size associated with one or more actionable peripheral nodes indicates a frequency of access by the clinician of the EMR in the set of EMRs;

receiving a selection of a first actionable peripheral node from the set of one or more actionable peripheral nodes, wherein the first actionable peripheral node represents the patient; and in response to receiving the selection of the first actionable peripheral node, displaying the actionable central node to represent the patient.

11. The media of claim 10, wherein the set of one or more actionable peripheral nodes is automatically updated in response to receiving the selection of the first time period and the second time period.

12. The media of claim 11, wherein a larger size indicates a higher frequency of access of the EMR associated with the patient during the selected first time period and second time period, and wherein a smaller size indicates a lesser frequency of access of the EMR associated with the patient during the selected first time period and second time period.

13. The media of claim 11, wherein a smaller size indicates a higher frequency of access of the EMR associated with the patient during the selected first time period and second time period, and wherein a larger size indicates a lesser frequency of access of the EMR associated with the patient during the selected first time period and second time period.

14. The media of claim 10, wherein each actionable peripheral node in the set of one or more actionable peripheral nodes is connected to the actionable central node by an arrow, each arrow pointing in a direction of access of the each actionable peripheral node's respective EMR.

15. The media of claim 10, further comprising one or more filters, each filter having a different criteria, wherein selection of the each filter restricts the set of one or more actionable peripheral nodes to a subset of the set of one or more actionable peripheral nodes that meet the criteria of the each selected filter.

16. The media of claim 15, wherein the criteria of the one or more filters comprises at least one of a gender, age, medication, or EMR access details.

17. The media of claim 15, wherein the criteria of the one or more filters comprises a location.

18. One or more non-transitory computer-storage media having computer-executable instructions embodied thereon that, when executed by a computing device, cause the computing device to perform a method for dynamically displaying a time-ordered sequence of audit events related to a clinician and a patient on a graphical user interface (GUI), for facilitating a reconstruction and examination of the time-ordered sequence of audit events, the method comprising:

receiving a request for a graphical representation of the time-ordered sequence of audit events related to the clinician;

in response to receiving the request, rendering the graphical representation on the GUI by utilizing data associated with a set of electronic medical records (EMRs) accessed by the clinician;

dynamically displaying on the GUI of the computing device, a first timeline configured to enable selection of a first time period within a first range, the first timeline comprising a first coarseness and a first bi-directional slider for receiving a selection of the first time period;

dynamically displaying on the GUI of the computing device, a second timeline having a second range corresponding to the first time period selected on the first timeline, the second timeline configured to enable selection of a second time period within the second range, the second timeline comprising a second coarseness finer than the first coarseness of the first timeline, a second bi-directional slider for receiving a selection of the second time period, and a third range corresponding to the second time period selected on the second timeline;

dynamically displaying on the GUI of the computing device, an actionable central node representing the clinician and a set of actionable peripheral nodes representing a set of patients associated with the set of EMRs accessed by the clinician during a specified time period, wherein the set of actionable peripheral nodes comprises a dynamic number of individual actionable peripheral nodes;

receiving a selection of the first time period;

in response to receiving the selection of the first time period, the dynamic number of the set of actionable peripheral nodes corresponds to the first time period, wherein each actionable peripheral node displayed on the GUI represents a patient in the set of patients having its EMR accessed by the clinician during the first time period, and wherein a size associated with each actionable peripheral node indicates a frequency of the patent having its EMR accessed by the clinician;

receiving a selection of at least one actionable peripheral node of the set of actionable peripheral nodes, the at least one actionable peripheral node representing a first patient; and in response to receiving the selection, replacing the actionable central node to represent the clinician and replacing the clinician and the first patient and replacing the set of actionable peripheral nodes with a clockwise timeline having one or more icons overlaid at points in time where the first patient's EMR was accessed by the clinician, the clockwise timeline having bounds corresponding to the selected first time period.

19. The media of claim 18, wherein each icon of the one or more icons represents a different type of audit event.

20. The media of claim 19, wherein interaction with each of the one or more icons initiates presentation of a patient-specific summary associated with the type of audit event represented by each of the one or more icons.

* * * * *